(12) United States Patent
Greiner-Stoeffele et al.

(10) Patent No.: US 9,856,470 B2
(45) Date of Patent: Jan. 2, 2018

(54) PROCESS FOR GENERATING A VARIANT LIBRARY OF DNA SEQUENCES

(75) Inventors: Thomas Greiner-Stoeffele, Leipzig (DE); Claudia Feller, Leipzig (DE); Marc Struhalla, Leipzig (DE)

(73) Assignee: c-LEcta GmbH, Leipzig (DE)

( * ) Notice: Subject to any disclaimer, the term of this patent is extended or adjusted under 35 U.S.C. 154(b) by 282 days.

(21) Appl. No.: 12/960,061

(22) Filed: Dec. 3, 2010

(65) Prior Publication Data

US 2011/0152126 A1 Jun. 23, 2011

Related U.S. Application Data

(63) Continuation of application No. PCT/EP2009/003945, filed on Jun. 3, 2009.

(30) Foreign Application Priority Data

Jun. 5, 2008 (EP) .................................... 08010256

(51) Int. Cl.
*C12Q 1/68* (2006.01)
*C12N 15/10* (2006.01)

(52) U.S. Cl.
CPC ....... *C12N 15/1093* (2013.01); *C12N 15/102* (2013.01)

(58) Field of Classification Search
None
See application file for complete search history.

(56) References Cited

U.S. PATENT DOCUMENTS

| 6,582,914 B1 * | 6/2003 | Caldwell .............. C12N 15/102 435/6.1 |
| 7,402,383 B2 * | 7/2008 | Bovenberg et al. .......... 435/6.12 |
| 2002/0048772 A1 * | 4/2002 | Dahiyat ................. C07K 1/047 435/7.1 |

FOREIGN PATENT DOCUMENTS

| EP | 0 466 083 A2 | 1/1992 |
| WO | WO 97/46670 A1 | 12/1997 |
| WO | WO 98/32845 A1 | 7/1998 |
| WO | WO 98/58080 A1 | 12/1998 |
| WO | WO 01/12802 A1 | 2/2001 |
| WO | WO 02/34762 A2 | 5/2002 |
| WO | WO 2006/047669 A2 | 5/2006 |

OTHER PUBLICATIONS

Ge et al., "Simultaneous Introduction of Multiple Mutations Using Overlap Extension PCR", Biotechniques, 1997, 22:28-30.*
Pogulis et al. (Methods in Molecular Biology, 1996, vol. 57, p. 167-176).*
Ling et al., "Approaches to DNA Mutagenesis: An Overview", Analytical Biochemistry, 1997, vol. 254, pp. 157-178 (twenty (22) sheets).
Horton et al., "Engineering Hybrid Genes Without the Use of Restriction Enzymes: Gene Splicing by Overlap Extension", Gene, 1989, vol. 77, pp. 61-68 (eight (8) sheets).
Shayiq et al., "Multiple in Vitro Site-Directed Mutagenesis Using Asymmetric Polymerase Chain Reaction", Analytical Biochemistry, Aug. 15, 1994, vol. 221, No. 1, pp. 206-208 (three (3) sheets).
Weisberg et al., "Simultaneous mutagenesis of multiple sites: application of the ligase chain reaction using PCR products instead of oligonucleotides", BioTechniques, Jul. 15, 1993, vol. 15, No. 1, pp. 68-70, 72-74, and 76 (seven (7) sheets).
Ito et al., "A general method for introducing a series of mutations into cloned DNA using the polymerase chain reaction", Gene, 1991, vol. 102, No. 1, pp. 67-70 (four (4) sheets).
Osuna et al., "Combinatorial mutagenesis of three major groove-contacting residues of EcoRI: single and double amino acid replacements retaining methyltransferase-sensitive activities", Gene, 1991, vol. 106, pp. 7-12 (six (6) sheets).

* cited by examiner

*Primary Examiner* — Stephanie K Mummert
(74) *Attorney, Agent, or Firm* — Agris & Von Natzmer, LLP; Joyce Von Natzmer

(57) ABSTRACT

A method for generating a variant library of DNA sequences starting from at least one DNA starting sequence and including the steps: a) selecting at least two mutation sites in the starting sequence; b) dividing the DNA starting sequence into at least two sequence segments such that at least two of these sequence segments each contain at least one of the mutation sites; c) amplifying the sequence segments by polymerase chain reaction using at least five different oligonucleotides, where at (i) least one of the oligonucleotides can attach to each mutation site; (ii) at least two of the oligonucleotides can attach to at least one mutation site, and (iii) mutations are introduced, via mismatch positions, into the PCR amplificates by the oligonucleotides at the mutation sites where at least two mutations are introduced at at least one of the mutation sites; and d) linking the amplificates to give DNA sequences.

10 Claims, 3 Drawing Sheets

PROCESS FOR GENERATING A VARIANT LIBRARY OF DNA SEQUENCES

CROSS REFERENCE TO RELATED APPLICATIONS

This application is a continuation of international patent application no. PCT/EP2009/003945, filed Jun. 3, 2009 designating the United States of America and published in German on Dec. 10, 2009 as WO 2009/146892 A1, the entire disclosure of which is incorporated herein by reference. Priority is claimed based on European patent application no. 08010256.9, filed Jun. 5, 2008.

BACKGROUND OF THE INVENTION

The invention relates to a method for generating a variant library of DNA sequences.

In the prior art, methods for generating certain individual variants of a DNA sequence are described, and reference can be made to, for example, L. Ge et al., Biotechniques, 22(1), 1997, 28-30; E. P. Weisberg et al., Biotechniques, 15(1), 1993, 68-76; R. M. Shayiq et al., Analytical Biochemistry, 221(1), 1994, 206-208; or W. Ito et al., Gene, 102(1), 1991, 67-70. In these methods, multiple mutations are introduced simultaneously into a DNA sequence. With PCR, individual fragments of a DNA sequence are generated and reconnected. Here, mutations are introduced via mismatch primers, and at each mutation site only one primer binds. However, this does not involve the generation of a variant library, but the creation of a certain individual variant of a DNA sequence.

Methods for generating a variant library of DNA sequences are likewise known in the prior art. In this regard, reference can be made to, for example, WO 01/12802, WO 02/34762, Wong T. S. et al., *The Diversity Challenge in Directed Protein Evolution, Combinatorial Chemistry & High Throughput Screening*, 9(4), 2006, 271-288; and C. Neylon, Nucleic Acids Research, 2004, 32(4), 1448-59.

WO 01/12802 and WO 02/34762 disclose methods for generating a variant library of DNA sequences. The methods use oligonucleotide mixtures and a certain type of PCR, such that at each mutation site only one primer binds. A division of the starting sequence into multiple sequence segments and amplification thereof are not carried out.

A further method known from the prior art is "DNA shuffling" (cf., for example, WO 98/32845, WO 98/58080, WO 2006/047669). Spatially separated segments are recombined with one another (shuffled). No mutations are introduced by oligonucleotides, and the oligonucleotides used also do not bind to mutation sites.

Proteins have a variety of applications in research and industry. Many technical applications for proteins make it necessary to adapt the properties of natural proteins to the particular requirements of the respective technical application. For this purpose, there are introduced into the proteins artificial modifications which achieve the desired improvement of a property of the protein. This approach is called "protein engineering".

The structural clarification of native proteins has led in recent years to the availability of detailed information about sequence, structure, and structure-activity relationships for a very large number of proteins. Nevertheless, attempts to modify the properties of proteins by means of rational protein design are often not successful. Use is often made of statistical methods in which mutagenesis methods are used to generate a variant library which comprises a large number of protein variants, which is then investigated with regard to protein variants having improved properties.

As a result of the detailed information about the structure of the native proteins, it appears meaningful in many cases to not subject the wild-type sequence to completely arbitrary mutagenesis, but to limit the mutations to certain amino acid positions of the protein (focused mutagenesis). As a result, the theoretically possible complexity of the library can be restricted. Thus, for example, it is possible to identify in proteins amino acid positions which are responsible for a certain binding capability or, in the case of enzymes, for substrate recognition. But also for more global properties such as protein stability, particularly relevant amino acid positions can be identified.

Likewise, it is desirable to limit the mutations permitted at individual amino acid positions to certain amino acid substitutions. For example, the sought-after target property of the modified protein allows a meaningful restriction of the permitted amino acids. A very plausible restriction of the permitted amino acid positions at individual positions can likewise be deduced from the comprehensive sequence data in sequence databases. Via sequence alignments, it is possible to identify for individual amino acid positions the amino acids which naturally occurring proteins have at this site. Accordingly, the amino acid substitutions at these positions can then be restricted in the mutagenesis to the naturally occurring amino acids.

When generating focused variants, it is thus desirable to achieve a very high degree of control, not only with regard to the relative location of the modifications within the entire sequence, but also with regard to the number of modifications per entire sequence and the types of modifications.

In the prior art, a range of mutagenesis methods are known. One simple possibility consists in carrying out error-prone PCR, in which a polymerase incorporates nucleotides into the DNA sequence incorrectly during the DNA amplification and, as a result, generates mutations. A further possibility for introducing mutations into DNA sequences is DNA shuffling.

Mutagenesis methods which function with the aid of oligonucleotides are also described. In this regard, reference can be made to, for example, WO 02/34762 and WO 01/12802. In general, such mutagenesis methods, with the aid of oligonucleotides, can introduce mutations into DNA sequences via mismatch positions. Thus, for example, all 20 natural amino acids can be inserted at an amino acid position with the aid of a randomized oligonucleotide (saturation mutagenesis). A particular embodiment of this type of mutagenesis is quickchange mutagenesis, which can also be carried out as multiple quickchange mutagenesis. A similar method describes massive mutagenesis. With both methods, small to large numbers of oligonucleotides are used in the polymerase-mediated amplification of a DNA sequence to be mutated. A disadvantage of both methods is that it is not possible to control how many oligonucleotides are used per amplicon. Individual mutation sites can be overlooked by the polymerase. As a result, the number of mutations per variant is subject to strong variations and cannot be controlled. The theoretical total complexity of the library can, as a result, not be sufficiently restricted. A further disadvantage occurs when a number of oligonucleotides can bind to one mutation site. Differences which are caused by a variance in the affinity of the oligonucleotides for the mutation site cannot be balanced out. A further disadvantage of the methods is the fact that the average number of mutations per variant having an increasing number of mutation sites is increasingly smaller than the number of mutation sites. As a result, libraries in which multiple mutations are intended to be combined can be generated only at very large complexities in which the proportion of variants which have the desired combination of multiple mutations makes up only a small fraction of the library. There is a need for methods for generating a variant library of DNA sequences,
in which the mutations can be restricted to a number of exactly determined positions of the DNA sequence (or protein sequence),
in which the mutation sites can be distributed across the entire DNA sequence,
in which it can be established which mutations are permitted at which position, which can be carried out easily and with standard laboratory methods,
in which the distribution of individual mutations in the library can be controlled very exactly,
in which neighboring mutations as well can be introduced in a controlled manner,
in which the total number of mutations per variant can be controlled exactly, and
in which the complexity of the library generated can be restricted with precision.

More particularly, there is a need for methods with which it is possible to generate variant libraries having a high proportion of variants in which multiple mutations are combined with one another.

SUMMARY OF THE INVENTION

An object of the invention is to provide a method for generating a variant library of DNA sequences which has advantages compared with the methods of the prior art, more particularly the abovementioned advantages.

This and other objects are achieved by the invention as described and claimed hereinafter.

The invention relates to a method for generating a variant library of DNA sequences starting from at least one DNA starting sequence, comprising the following steps:
a) selecting at least two mutation sites in the DNA starting sequence;
b) dividing the DNA starting sequence into at least two sequence segments in such a way that at least two of these sequence segments each comprise at least one of the mutation sites;
c) amplifying the sequence segments by PCR with the aid of at least five different oligonucleotides in total, wherein
  (i) at least one of the oligonucleotides can attach to each mutation site;
  (ii) at least two of the oligonucleotides can attach to at least one mutation site; and
  (iii) in the amplification products (fragments) obtained by PCR, mutations are introduced by the oligonucleotides at the mutation sites via mismatch positions, wherein at least one mutation site, at least two mutations are introduced; and
d) linking the amplification products to form DNA sequences.

The method according to the invention is preferably a mutagenesis method, but not a recombination method. For the purpose of the invention, a mutagenesis method is understood to mean the generation of a large number of variants, preferably starting from a DNA starting sequence. Mutagenesis methods can be differentiated from recombination methods, in which a number of variants of a DNA sequence are combined with one another.

For the purpose of the method according to the invention, "attach to" means that the base pairing between the sequence segment and oligonucleotide results in a sufficiently stable complex which can serve as a starting point for PCR. Usually, the oligonucleotide for this purpose binds to the sequence segment via multiple nucleobases, with the mutation site being flanked on both sides by the double strand formed. It is not necessary for all nucleotides of the oligonucleotide to be involved in the binding. As the case may be, the mismatch positions present then introduce site-directed mutations in the course of the PCR. Furthermore, via 5' overhangs, sequence extensions are possible for the oligonucleotides, which enable a subsequent linking of the sequence segments.

The method according to the invention is suitable for producing a variant library of DNA sequences. These DNA sequences can then be translated into a variant library of protein molecules in which targeted mutations are introduced at defined amino acid positions. The method according to the invention is preferably carried out in a targeted manner, i.e., proceeds in a directed manner, in a rational manner, in a carefully considered manner, or predetermined to a certain degree, at least in part, but not arbitrarily or randomly (randomized). This relates especially particularly to the selection of the at least two mutation sites in the DNA starting sequence according to step (a), to the (notional) division into two sequence segments according to step (b), and/or to the selection of the at least five different oligonucleotides in step (c).

The method according to the invention differs in this way from those methods of the prior art which proceed in a randomized manner (e.g., with the aid of *E. coli* XL1 red, UV irradiation, chemical mutagenesis such as deamination or alkylation, DNA shuffling, or error-prone PCR).

Since the mutations in the method according to the invention are introduced at the mutation sites via mismatch positions, the method according to the invention is based on the principle of site-directed mutagenesis. Therein, the method according to the invention differs from those methods of the prior art which are based on DNA shuffling or on error-prone PCR.

In the prior art, site-directed random mutagenesis is also known, in which PCR is carried out with the aid of partially degenerate primers. With degenerate primers, nucleotide mixtures are used in the synthesis of the primers. Preferably, however, such degenerate primers (oligonucleotides) are not used in the method according to the invention, i.e., a randomized sequence segment is not present on the oligonucleotides.

The method draws on established methods in molecular biology. Point mutations can be introduced, via oligonucleotides, by PCR amplification (site-directed mutagenesis). The resulting fragments can be linked together again by PCR or by restriction enzymes and ligases. In this regard, reference can be made to, for example, S. Brakmann et al., *Directed Molecular Evolution of Proteins*, VCH-Wiley, 1st edition, 2002; F. H. Arnold, *Directed Enzyme Evolution: Screening and Selection Methods*, Humana Press, 1st edition, 2003.

With the method according to the invention, it is possible, from multiple sequence segments containing mutation sites, to generate fragments separately which then have mutations at the respective mutation sites.

It is also possible with the method according to the invention, starting from an individual sequence segment containing at least one mutation site, to generate in parallel multiple different fragments which differ by the type of the respective mutation at this mutation site. This is achieved by different oligonucleotides, which function as primers in the amplification by PCR, being able to attach at the same mutation site and generating, however, different mutations by means of different mismatch positions. By generating the PCR fragments in parallel, the fragments can be quantified after generation and then mixed in an exactly controlled ratio. As a result, unwanted imbalances in the mutation distribution are avoided at the corresponding mutation site. When the DNA fragment contains only one mutation site and when, for example, 20 mutations are intended to be introduced at this mutation site, 20 PCR reactions should be carried out in parallel. When two mutation sites are present on the fragment, all possible combinations of the mutations should be carried out in parallel at both mutation sites. Certainly, the oligonucleotides can also be used as a mixture in the PCR reactions, but as a result imbalances in the mutation distribution need to be taken into account. In order to avoid too high a number of PCR fragments, the next mutation site in the DNA sequence can also be moved to the next DNA fragment. When no oligonucleotide mixtures are used, it is nevertheless generally possible, with a few dozen PCR reactions carried out in parallel, to generate a variant library having complexities of more than 100 000 variants up to libraries having more than 1 million variants.

In one preferred embodiment, the method according to the invention is used to generate a DNA library encoding a library of protein variants having modified binding properties or, in the case of an enzyme, having a modified substrate specificity. The mutation sites are restricted to amino acid positions which, deduced from structural data or structural models, are responsible for ligand recognition in the case of a binding protein (e.g., antibody) or substrate recognition in the case of an enzyme. For example, the mutagenesis can be focused on those amino acid positions in the substrate-binding pocket of an enzyme which may be responsible for substrate binding and which are not catalytic amino acid residues.

In another preferred embodiment, only those amino acids which also occur in natural protein sequences are permitted at the selected mutation sites. These amino acids can be identified via sequence comparisons with sequence databases. Homology comparisons of the starting sequence make it possible, in sequence alignments for individual amino acid positions, to identify those amino acids which occur at this site in other proteins. This is a method with which the diversity of nature can be reproduced in the selected positions in the variant library to be generated.

It has surprisingly been found that the mutation distributions of the resulting variant libraries can be controlled very exactly with the method according to the invention. For example, it is possible for all variants of the variant library to have the same number of mutations. The occurrence of nonmutant sequences (wild type) can be excluded, or controlled very exactly. When, for example, 6 mutations are to be introduced per protein, it is easily possible for the largest part of the variant library to actually have 6 mutations as well. Variants having 7 mutations are not present. The variance of the number of mutations per variant can be controlled very exactly. It is thus possible, for example, to also establish how many variants are supposed to have approximately 5 mutations, and so on.

A feature of the PCR-based mutagenesis methods described in the prior art for generating variant libraries is that the number of mutations per variant is generally subject to a normal distribution. There is a fraction of variants in the library having a certain mutation number which occurs most often. However, these libraries also contain variants which have more mutations and variants which have fewer mutations. The mutation distribution cannot be restricted and the total complexity of the libraries cannot be adequately limited. When a variant library at, for example, 5 amino acid positions is completely randomized, this results in, for these variants, a complexity of $20^5=3.2$ million variants. For 6 amino acid positions, this results in $20^6=64$ million variants, and for 7 amino acid positions, this results in $20^7=1.28$ billion variants. When the PCR-based methods described in the prior art are used to generate a variant library having mainly 5 amino acid mutations, this also results in fractions having 6 and 7 amino acid substitutions. In addition, this results in numerous variants which have fewer than 5 amino acid substitutions. Usually, the largest fraction with regard to the number of mutations makes up about 20 to 40% of the library generated. A large proportion of the library thus does not have the desired number of mutations. Furthermore, the theoretical total complexity of the library cannot be adequately restricted. It is, for example, not desirable to generate a library having a theoretical complexity of more than 1 billion variants when subsequently only a few 100 000 thereof can be analyzed.

The method according to the invention allows the generation of variants of a DNA sequence in which the above-described disadvantageous mutation distribution can be avoided. The method allows the generation of a variant library in which the number of mutations N per variant is the same for each variant. Here, preferably $2 \leq N \leq 20$, more preferably $3 \leq N \leq 10$, and most preferably $4 \leq N \leq 8$.

Likewise, it is possible to generate variant libraries in which the library does not contain any variants which have more than 2 mutations, with preference more than 1 mutation, more than the number of mutations of the largest fraction of the variants. When the number of mutations of the largest fraction is, for example, 5, the library preferably does not contain any variants which have more than 7 mutations, with preference more than 6 mutations.

Using the method according to the invention it is possible to generate variant libraries in which the mutation sites can be distributed across the entire DNA sequence. Preferably, at least two mutation sites of the variant library have an interval of preferably at least 30 nucleotides, more preferably at least 100 nucleotides, even more preferably at least 200 nucleotides, yet even more preferably at least 300 nucleotides, and in particular at least 500 nucleotides. In an especially preferred embodiment, three mutation sites of the variant library are distributed on the DNA sequence such that the interval between the first and the second mutation site, and also the interval between the second and the third mutation site, is in each case at least 30 nucleotides, more preferably at least 50 nucleotides, even more preferably at least 100 nucleotides, yet even more preferably at least 150 nucleotides, and in particular at least 200 nucleotides.

The method according to the invention allows the creation of variant libraries in which the theoretical total complexity can be adequately restricted without the average number of mutations having to be reduced as a result. For example, it is easily possible to produce a library which has a theoretical complexity of less than 100 000 and in which, nevertheless, more than 75% of the variants have more than 5 mutations.

The method according to the invention pursues the goal of generating a variant library of DNA sequences. The variant library, according to its definition, does not comprise any individual variants, but a multiplicity of different variants of DNA sequences. In this respect, the method according to the invention differs from methods of the prior art which have the generation of an individual species (variant) as their goal. Likewise, the method according to the invention differs from methods of the prior art which have the recombination of individual variants of DNA sequences as their goal. Preferably, the method according to the invention pursues the goal of generating a variant library having at least $10^1$, more preferably at least $10^2$, even more preferably at least $10^3$, yet even more preferably at least $10^4$, and in particular at least $10^5$ different DNA sequences.

For the purpose of the invention, a mutation site is preferably a partial sequence of the starting sequence, to which one of the oligonucleotides used in the PCR amplification binds in the course of the method according to the invention and which is subjected to a sequence modification. A mutation site can be mutated multiple times in the course of the method according to the invention, i.e., comprise multiple mutations. The mutations can be introduced at multiple positions within a mutation site. The sequence positions which are being modified do not necessarily have to be within the binding sequence of an oligonucleotide, but these will be generally at least directly adjacent. The modified sequence is, in any case, part of the mutation site. It is possible for the sequences of two mutation sites to overlap with regard to the binding sequence of the oligonucleotides. When multiple oligonucleotides which compete with one another and which act at the same mutation location are used in the course of the method according to the invention, these oligonucleotide groups are assigned to a mutation site.

For the purpose of the invention, a mutation is preferably a modification of the DNA sequence at a certain position. The mutation preferably relates to the DNA level, i.e., preferably not to the protein level which this DNA encodes as the case may be. A mutation can consist:

in the substitution of one nucleotide or in the substitution of two or three nucleotides immediately following one another in the DNA starting sequence;

in the deletion of one nucleotide; or in the deletion of multiple, preferably three, six, or nine, nucleotides immediately following one another in the DNA starting sequence; and/or in the insertion of one nucleotide; or in the insertion of multiple, preferably three, six, or nine, nucleotides immediately following one another in the DNA starting sequence.

Substitution, insertion, and deletion are known to a person skilled in the art. These mutations can be clearly identified by comparison of the DNA starting sequence with the sequence of the amplification product, with the nonmutant starting sequence serving as the reference.

A mutation position for the purpose of the method according to the invention is understood to mean the sequence regions at which a certain mutation is effective. In the case of substitutions, the mutation positions can be specified by naming the nucleotide positions concerned in the starting sequence. In the case of insertions, the mutation positions can be specified by naming the two nucleotide positions between which the insertion lies. In the case of deletions, the mutation positions can be specified by naming the deleted nucleotide positions.

An individual substitution mutation relates to individual nucleotides or up to three nucleotides immediately following one another within the sequence in the DNA starting sequence, but not to multiple nucleotides which are separated within the sequence by at least 1 nucleotide which, for its part, is not subjected to any mutation. When a mutation is carried out on two nucleotides which are separated from one another only by a single nucleotide and when both nucleotides belong to a triplet encoding an amino acid, both nucleotides are preferably regarded as a single mutation. The determination of whether two nucleotides which are separated from one another only by a single nucleotide belong to a triplet encoding an amino acid is known to a person skilled in the art and is usually guided by the reading frame, through which the start codon of a gene sequence is established.

When multiple substitutions, deletions, or insertions are introduced at one mutation position of the DNA sequence, the corresponding mutations are consolidated as a group of mutations which become effective at the same position.

A variant fraction for the purpose of the present invention is defined via the number of mutations for the respective variants. All variants having a certain number of mutations are subsumed under one fraction. Variants each having, for example, six mutations thus belong to the same variant fraction. The size of a variant fraction is measured by the absolute number of different variants which belong to this fraction. Identical species, i.e., variants having identical sequences, thus do not increase the size of the variant fraction.

Library complexity is, for the purpose of the present invention, distinguished between theoretical and physical complexity. Theoretical complexity corresponds to the sum of all possible variants which are possible when carrying out the mutagenesis. Physical complexity corresponds to the number of variants which are actually generated when carrying out the mutagenesis.

With the aid of the method according to the invention, the theoretical complexity of the variant library can be restricted very well, and it is possible as a result to generate variant libraries having large physical complexities, such that the theoretical complexity of the database is not that much greater than the physical complexity. The physical complexity of variant libraries generated in the course of the method according to the invention is preferably greater than 10 000, more preferably greater than 50 000, even more preferably greater than 100 000, yet even more preferably greater than 500 000, and in particular greater than 1 000 000, and the theoretical complexity is preferably less than 50 times, more preferably less than 25 times, even more preferably less than 10 times, even more preferably less than 5 times, yet even more preferably less than 3 times, and in particular less than 2 times the physical complexity of the library generated. In a preferred embodiment, the theoretical complexity is just as great as the physical complexity of the library.

In the case of methods for undirected mutagenesis of a DNA sequence, the theoretical complexity is very difficult to calculate. A feature of the libraries generated is the above-described disadvantageous mutation distributions, with each variant fraction having different theoretical complexities. The variant fraction having 2 mutations from a library of a gene which comprises 200 amino acid codons has a theoretical complexity of about 65 million variants when all possible 19 amino acid substitutions are possible in each case. The fraction having three mutations has, in contrast, a theoretical complexity of about 246 billion variants.

In the case of a directed mutagenesis, the theoretical complexity for the purpose of the method according to the invention corresponds to the number of possible combinations of permissible mutations in the library.

In one preferred embodiment, the mutations in a mutation site at the DNA level are restricted to an individual triplet which encodes a certain amino acid in the DNA starting sequence at the protein level.

Oligonucleotides are known to persons skilled in the art. For the purpose of the description, oligonucleotides are preferably oligodeoxyribonucleotides of the four deoxyribonucleotides deoxyadenosine, deoxyguanosine, deoxycytidine, and deoxythymidine. These oligonucleotides are commercially available and can in principle be produced in any sequence using methods which are known to persons skilled in the art, for example in solid-phase syntheses with the aid of suitable synthesis robots starting from phosphoramidites. In this regard, see, for example, C. W. Dieffenbach et al., *PCR Primer: A Laboratory Manual*, Cold Spring Harbor Laboratory Press, 2nd edition, 2003.

In one preferred embodiment, a nucleotide mixture is used in at least one position in the production of the oligonucleotides, so that this position is randomized. When a mixture of all four oligodeoxyribonucleotides or the corresponding phosphoramidites is used, this generates at one randomized position four different oligonucleotides in total which differ from one another at least in this position. In the case of two positions which are each completely randomized, 16 different oligonucleotides in total are correspondingly generated. During the amplification by means of PCR, these oligonucleotides then compete for the same mutation site and introduce a mutation there, depending on whether it involves a match position or a mismatch position. When a mixture of all four oligodeoxyribonucleotides or the corresponding phosphoramidites was used at one position in the synthesis of the oligonucleotides, one resulting oligonucleotide is inevitably a match oligonucleotide and the remaining three oligonucleotides are mismatch oligonucleotides.

For the purpose of the method according to the invention, "PCR" is understood to mean a method for amplifying a DNA sequence (the starting sequence), in which at least two primers are used to multiply a defined sequence region by means of a DNA polymerase by cyclic repetitions of denaturation, annealing, and elongation steps, and the primers flank the amplifying sequence region and attach to the corresponding region of the starting sequence. The amplification of DNA sequence segments by PCR is known to a person skilled in the art, and also overlap extension PCR (also sometimes referred to as "splicing by overlap extension PCR", SOE-PCR) and outside cutter among others. In this regard, reference can be made in full to, for example, M. J. McPherson et al., PCR (The Basics), Taylor & Francis, 2nd edition, 2006; and M. Altshuler, *PCR Troubleshooting: The Essential Guide*, Caister Academic Press, 2006.

In step a) of the method according to the invention, at least two mutation sites are selected in the DNA starting sequence.

The total number m of mutation sites in the DNA starting sequence is, in principle, freely selectable. It can be m≥2, ≥3, or ≥4, preferably m≥5, ≥6, or ≥7, more preferably m≥8, ≥9, or ≥10, even more preferably m≥11, ≥12, or ≥13, most preferably m≥14, ≥15, or ≥16.

DNA starting sequence is understood to mean, for the purpose of the description, preferably a DNA sequence which can be native (wild-type sequence), but it does not necessarily have to be native. The method according to the invention can also start from multiple different DNA starting sequences. Preferably, the method according to the invention starts from an individual DNA starting sequence.

The DNA starting sequence can, in principle, have any sequence length. Preferably, the DNA starting sequence comprises from 50 to 10 000 nucleotides, more preferably from 100 to 5000 nucleotides, even more preferably from 200 to 3000 nucleotides, yet even more preferably from 300 to 2500 nucleotides, and in particular from 400 to 2000 nucleotides.

In a preferred embodiment, the DNA starting sequence does not comprise a stop codon (UAA, UAG, UGA) within a given reading frame. The reading frame is usually given by the start codon of a gene sequence.

Preferably, the DNA starting sequence encodes a protein, particularly preferably an enzyme. Preferably, the enzyme is selected from the group consisting of: 1. Oxidoreductases; 2. Transferases; 3. Hydrolases; 4. Lyases; 5. Isomerases; and 6. Ligases.

Preferred oxidoreductases are selected from the EC group consisting of 1.1, 1.2, 1.3, 1.4, 1.5, 1.6, 1.7, 1.8, 1.9, 1.10, 1.11, 1.12, 1.13, 1.14, 1.15, 1.16, 1.17, 1.18, 1.19, and 1.97.

Preferred transferases are selected from the EC group consisting of 2.1, 2.2, 2.3, 2.4, 2.5, 2.6, 2.7, 2.8, and 2.9.

Preferred hydrolases are selected from the EC group consisting of 3.1, 3.2, 3.3, 3.4, 3.5, 3.6, 3.7, 3.8, 3.9, 3.10, 3.11, and 3.12.

Preferred lyases are selected from the EC group consisting of 4.1, 4.2, 4.3, 4.4, 4.5, 4.6, and 4.99.

Preferred isomerases are selected from the EC group consisting of 5.1, 5.2, 5.3, 5.4, 5.5, and 5.99.

Preferred ligases are selected from the EC group consisting of 6.1, 6.2, 6.3, 6.4, and 6.5.

The EC nomenclature introduced by the International Union of Biochemistry and Molecular Biology (IUBMB) is known to a person skilled in the art. Information concerning this can be found on the website of the IUBMB.

In step b) of the method according to the invention, the DNA starting sequence is divided into k sequence segments, where k is at least 2. Preferably k≥3, more preferably k≥4, even more preferably k≥5, yet even more preferably k≥6, and in particular k≥8.

The division is preferably carried out purely notionally, i.e., preferably no cleavage of the DNA starting sequence takes place (e.g., with restriction endonucleases). Preferably, the notionally divided sequence segments are amplified separately in step c) by PCR. The selection of suitable primers enables the separate amplification of the individual sequence segments, resulting ultimately in individual fragments of the DNA starting sequence (which carry mutations now and then).

The sequence segments are established such that at least two sequence segments each comprise at least one mutation site. The k sequence segments can therefore be divided in principle into the following groups:
- g sequence segments $S_0$, which do not comprise any mutation sites; and
- h sequence segments $S_{>0}$, which comprise at least one mutation site.

The group of h sequence segments $S_{>0}$, which comprise at least one mutation site, can, in turn, be further divided into:
- i sequence segments $S_1$, which comprise one mutation site; and
- j sequence segments $S_{>1}$, which comprise multiple, preferably 2, mutation sites.

The entirety of all sequence segments k is thus put together as follows:

$$k=g+h=g+i+j.$$

Preferably, g>h, g=h, or g<h.

In one preferred embodiment of the method according to the invention, g=0 (then, in this case: k=h). In another preferred embodiment of the method according to the invention, g≥1, more preferably g≥2, even more preferably g≥3, yet even more preferably g≥4, and in particular g≥5.

In the method according to the invention, preferably h≥2. Preferably, h≥3, more preferably h≥4, even more preferably h≥5, yet even more preferably h≥6, and in particular h≥7.

Preferably, i>j, i=j, or i<j.

In one preferred embodiment of the method according to the invention, i=0 (then, in this case: h=j). In another preferred embodiment of the method according to the invention, i≥1, more preferably i≥2, even more preferably i≥3, yet even more preferably i≥4, and in particular i≥5.

In the method according to the invention, preferably j≥1. Preferably, j≥2, more preferably j≥3, even more preferably j≥4, yet even more preferably j≥5, and in particular j≥6.

The establishment of the relative location of the individual sequence segments on the DNA starting sequence can, in principle, be carried out in any way. Since the mutations are introduced at the mutation sites by means of mismatch positions during the amplification by PCR, the sequence segments are preferably established such that the mutation sites are located where the oligonucleotides (primers) bind during the PCR, i.e., near the 5' or 3' end of the respective sequence segments.

Further considerations may play a role in establishing the relative location of the individual sequence segments. These considerations are familiar to a person skilled in the art and result from, for example, carrying out PCR or subsequent processing of the amplification products. Thus, it is generally preferred in PCR, for example, when the GC content within the primer sequence does not exceed 50%. Also certain recognition sequences of commercially available restriction endonucleases may play a role, since these enzymes may be used to subsequently generate, for example, sticky ends, which can be advantageous for the subsequent ligation in step d). In principle, the method according to the invention allows any partitioning of the DNA sequence into sequence segments. Generally, the position of the individual mutation sites determines the division of the DNA sequence into sequence segments.

The sequence length of the individual sequence segments $S_0$, $S_1$, or $S_{>1}$ can, in principle, be freely selected.

Preferably, each sequence segment comprises at least 48 nucleotides, more preferably at least 80 nucleotides, even more preferably at least 120 nucleotides, yet even more preferably at least 150 nucleotides, and in particular at least 200 nucleotides.

Preferably, each sequence segment comprises not more than 10 000 nucleotides, more preferably not more than 8000 nucleotides, even more preferably not more than 7000 nucleotides, yet even more preferably not more than 6000 nucleotides, and in particular not more than 5000 nucleotides. In the method according to the invention, the at least five different oligonucleotides in total usually function as primers in the amplification by PCR.

The total number of different oligonucleotides p is preferably p≥10, more preferably p≥15, even more preferably p≥20, yet even more preferably p≥30, and in particular p≥40.

The oligonucleotides preferably each have a sequence length of from 15 to 100 nucleotides, preferably from 20 to 80, even more preferably from 25 to 60, yet even more preferably from 27 to 50, and in particular from 30 to 45.

With regard to a first property, the oligonucleotides can, in principle, be divided into the following groups:
 oligonucleotides which bind to the 5' end of a sequence segment on the DNA starting sequence, i.e., are, to the 5' end of a sequence segment on the DNA starting sequence (parental strand), complementary (match or mismatch) (="sense primer" or "5' primer"); and
 oligonucleotides which bind to the 3' end of a sequence segment on the DNA starting sequence, i.e., are, to the 5' end of the complementary sequence segment on the DNA starting sequence (daughter strand), complementary (match or mismatch) (="antisense primer" or "3' primer").

Since at least two primers are needed in each case for each sequence segment to be amplified, viz. a sense primer in each case and an antisense primer in each case, the amplification of k sequence segments in total on the DNA starting sequence usually needs at least k sense primers and k antisense primers, i.e., 2k different oligonucleotides in total.

Since, in the method according to the invention, at least two of the oligonucleotides can attach to at least one mutation site of a sequence segment (cf. step c) (ii)), there is a kind of competitive situation for these sense primers and/or antisense primers. In addition to the 2k different oligonucleotides, there are therefore additionally a further l different oligonucleotides in total which are in competition with at least one of the 2k oligonucleotides (and, as the case may be, among one another as well), i.e., can bind to the same binding site on the sequence segment.

The total number of different oligonucleotides p is therefore usually given by the following relationship: p=2k+l.

For the purpose of the description, "competition" in this regard does not necessarily mean that the individual oligonucleotides are present next to one another at the same time in competition and have to compete for a common binding site on a certain sequence segment. Thus, the individual oligonucleotides may also be contacted individually in separate vessels with an identical sequence segment in each case, and the amplification products (fragments) thus obtained separately by PCR are later mixed with one another as appropriate.

In one preferred embodiment, in the method according to the invention, the number of oligonucleotides which can attach to one mutation site is identical to the number of amino acids which are allowed at the corresponding position in the resulting protein library.

Preferably, in the method according to the invention, mixtures of oligonucleotides which attach to the same binding site are not used. Preferably, in the generation of sequence segment fragments, all possible combinations of sense and antisense primers are used in separate, independent PCR reactions.

In the simplest embodiment of the method according to the invention, the DNA starting sequence is divided into two sequence segments (cf. step b)), and so k=2. The amplification of these two sequence segments requires 2k, i.e., 4, different oligonucleotides as primers, of which 2 oligonucleotides function as sense primers and the other 2 oligonucleotides function as antisense primers. In the simplest embodiment of the method according to the invention, it is possible for 2 oligonucleotides to attach to one mutation site of a sequence segment which comprises at least this one mutation site (competitive situation), of which the first oligonucleotide is among the abovementioned 2k oligonucleotides and the second oligonucleotide is considered by l=1. The total number of oligonucleotides p is thus given by p=4+1=5.

In one preferred embodiment of the method according to the invention, l≥2, more preferably ≥5, ≥6, or ≥7, even more preferably ≥8, ≥9, or ≥10, yet even more preferably ≥15, ≥20, or ≥25, and in particular ≥30, ≥40, or ≥50.

With regard to a second property, the oligonucleotides can, in principle, be divided into the following groups:
 oligonucleotides which do not contain any mismatch positions, i.e., generate no mutations during the amplification by PCR (="match oligonucleotides"); and oligonucleotides which contain at least one mismatch position, i.e., generate at least one mutation during the amplification by PCR and, consequently, can attach to one mutation site (="mismatch oligonucleotides").

For the purpose of the description, "match" preferably means that the nucleotide concerned is complementary to the DNA starting sequence, and "mismatch" preferably means that the nucleotide concerned is not fully complementary to the DNA starting sequence.

In one preferred embodiment of the method according to the invention, the total number of match oligonucleotides is greater than the total number of mismatch oligonucleotides. In another preferred embodiment of the method according to the invention, the total number of match oligonucleotides is less than the total number of mismatch oligonucleotides.

A person skilled in the art realizes that, depending on the type of sequence segments S for the amplification by PCR, a certain number of match or mismatch oligonucleotides is necessary. For example, for the g sequence segments $S_0$ of the DNA starting sequence, which do not comprise any mutation sites, 2 g match oligonucleotides are needed in the amplification by PCR. Analogously, for the i sequence segments $S_1$, which comprise a mutation site, (at least) i mismatch oligonucleotides and i match oligonucleotides are needed.

The mismatch oligonucleotides can, in turn, be divided into the following groups:
mismatch oligonucleotides which introduce one mutation (="single-mismatch oligonucleotides"); and
mismatch oligonucleotides which introduce multiple mutations ("multiple-mismatch oligonucleotides").

In a preferred embodiment of the method according to the invention, the number of single-mismatch oligonucleotides is greater than the number of multiple-mismatch oligonucleotides. In another preferred embodiment of the method according to the invention, the number of single-mismatch oligonucleotides is less than the number of multiple-mismatch oligonucleotides. In a further preferred embodiment, only single-mismatch oligonucleotides are used.

The k sequence segments contain the m mutation sites. Preferably, the mutation sites are more or less evenly distributed across the sequence segments. Preferably, each sequence segment contains, independently of one another, from 0 to 2 mutation sites, preferably from 1 to 2 mutation sites, even more preferably exactly 2 mutation sites.

In step c) of the method according to the invention, the sequence segments are amplified by PCR. The amplification of the different mutant variants of the sequence segments can be carried out together or in a spatially separated manner. In a preferred embodiment, at least one individual PCR is carried out per sequence segment, which can take place in a spatially separated manner from the amplification of the remaining sequence segments. In this respect, it is significant how many mutation sites are present on a sequence segment, since these mutation sites are then preferably present on the same sequence segment in PCR and are spatially separated, as the case may be, from the remaining sequence segments and the mutation sites lying thereon.

For the PCR, all polymerases are suitable in principle, for example the commercially available Taq polymerase, Vent polymerase, or Pfu polymerase.

In a preferred embodiment, the PCR makes use of polymerases whose proofreading function is restricted or fully suppressed ("error-prone polymerase"). In this way, the PCR results in the introduction of further mutations which are not necessarily present at the mutation sites. By using such polymerases, it is possible to generate variants whose number of mutation positions is distinctly greater than the number of mutation sites established on the DNA starting sequence.

In one preferred embodiment, the sequence segments are amplified in a spatially separated manner. For this purpose, preferably multiple identical DNA starting sequences are distributed into different vessels or compartments of a vessel and, in each vessel/compartment, a certain sequence segment is amplified using suitable oligonucleotides (at least one sense primer and one antisense primer). The removal of the amplification products (fragments) thus obtained, which carry mutations as the case may be, from the DNA starting sequence can be carried out with the aid of customary methods, for example by gel extraction after electrophoretic separation or by gel filtration or ion-exchange chromatography.

In a preferred embodiment, the amplification of the different mutant variants of individual sequence segments likewise takes place in a spatially separated manner. For this purpose, the possible oligonucleotide combinations for a certain sequence segment are used separately or in pooled groups in separate vessels/compartments for the PCR amplification.

Preferably, at least 2 variants, more preferably at least 3 variants, and in particular at least 4 variants, of at least one sequence segment, preferably at least two sequence segments, and in particular at least three sequence segments, are amplified in each case in a spatially separated manner.

In the method according to the invention at least one of the oligonucleotides can attach to each mutation site. Thus, this ensures that mutations can be introduced at the mutation sites via mismatch positions. It is also possible for multiple oligonucleotides to be able to attach to the same mutation site and be in competition with one another. When mismatch oligonucleotides are involved, they then insert different mutations. When a match oligonucleotide is also present in a competitive ratio, this generates not only the mutants but also amplification products (fragments) which correspond to the starting sequence or are completely complementary thereto. In the method according to the invention at least two of the oligonucleotides can attach to at least one mutation site.

When multiple oligonucleotides are in competition with one another with regard to one mutation site, they can be used together or separately from one another.

In one preferred embodiment, the competing oligonucleotides are distributed into different vessels and, in each vessel, the same sequence segment is amplified with the aid of the respective oligonucleotide in the absence of the other competing oligonucleotides. In this embodiment, the amplification products (fragments) generated for a sequence segment are preferably mixed before they are added in step d) of the method according to the invention. Optionally, the amplification products are quantified before mixing.

Individual steps of the method according to the invention can therefore be carried out in a spatially separated manner in various ways. Firstly, the individual sequence segments can be amplified separately from another by PCR; secondly, however, those sequence segments, as the case may also be, which contain mutation sites which multiple oligonucleotides compete for can also be amplified in a spatially separated manner with, in each case, an individual oligonucleotide (or else only a portion of the total competing oligonucleotides).

In one preferred embodiment of the method according to the invention, the DNA fragments generated separately from another are quantified before mixing. The quantification of the DNA fragments can be carried out with customary methods. For example, by the densitometric analysis of DNA agarose gels, by photometric determination of the absorbance of the DNA solution at 260 nm, or by fluorescence methods (for example, with intercalating fluorescent dyes, such as ethidium bromide or SYBR Green).

In the method according to the invention, in the amplification products obtained by PCR, mutations are introduced by the oligonucleotides at the mutation sites via mismatch positions. By means of an oligonucleotide, it is also possible to introduce mutations at multiple positions. In a preferred embodiment, at least two mutations are introduced in each case by at least one, preferably at least two, more preferably at least three, even more preferably at least four, yet even more preferably at least five, and in particular at least six, oligonucleotides.

In one preferred embodiment of the method according to the invention, oligonucleotides which can attach to the same mutation site are used as a mixture in a PCR reaction. In this case, there is an immediate competitive situation. Since the number and type of mismatch positions decides the affinity of the oligonucleotides for the sequence segment, the competing oligonucleotides may differ in their affinity, and this may have negative effects on the uniformity of the amplification products generated. More poorly binding oligonucleotides function statistically less often as primers and the corresponding mutations occur comparatively less often.

In another preferred embodiment of the method according to the invention, oligonucleotides which can attach to the same mutation site are used in separate PCR reactions and the PCR products obtained are subsequently mixed. Particularly preferably, oligonucleotides which are able to attach to the same mutation site are used in separate PCR reactions, the PCR products obtained are subsequently mixed at a certain ratio and, as a result, the ratio of the mutations introduced by the oligonucleotides in the variant library is controlled.

In step d) of the method according to the invention, the amplification products (fragments) are linked to one another again in the correct order. This can occur in different ways.

In one preferred embodiment, step d) is carried out by means of overlap extension PCR. Here, consecutive PCR fragments are generated such that they have identical sequence segments at their ends. When these PCR fragments are used together in a following PCR, the complementary ends of the fragments can assemble and be extended by the DNA polymerase used. As a result, the PCR fragments are linked to one another. In such an overlap extension PCR, multiple PCR fragments can be linked to one another at the same time.

In another preferred embodiment, restriction endonucleases are used to generate sticky ends at the ends of the PCR fragments to be linked, i.e., short oligonucleotide overhangs via which the individual fragments can then be specifically linked with the aid of DNA ligases. The recognition sites for the restriction endonucleases for generating the sticky ends can be introduced in the PCR via 5' overhangs of the primers. When use is made of type II restriction endonucleases which cut the DNA within its recognition sequence, it should be noted that the DNA sequences arising after ligation will generally differ from the original starting sequence. Corresponding translations of the DNA sequences into proteins may lead to modifications of the amino acid sequence. Particular preference is therefore given to the use of type IIS (outside cutter) restriction enzymes. These are restriction endonucleases which recognize asymmetric recognition sequences and cut outside their recognition sequence. With the aid of outside cutters, it is possible, via 5' overhangs of the primers and subsequent restriction digestion, to link two consecutive PCR fragments of a DNA sequence to one another via sticky ends, without modifying the DNA starting sequence at the connection site. There are also outside cutters which generate blunt ends. When two PCR fragments are linked via blunt ends, it is possible to connect two PCR fragments such that two mutations lie directly next to one another above and below the connection site. Thus, for example, two consecutive amino acid positions in a protein sequence can be mutated without these having to be part of a common mutation site. When the blunt ends of at least one fragment to be linked in the first ligation reaction are not introduced with an outside cutter, it is possible, by means of a variation of the approach, to even generate 4 consecutive mutations at one connection site, without using multiple mismatch oligonucleotides in the process.

In one preferred embodiment, the linking of the sequence segments is carried out stepwise. Here, individual sequence segments are initially linked independently of one another so that intermediate products are initially generated, which are then, in turn, linked to one another. When a DNA sequence is divided into, for example, 8 sequence segments, 2 sequence segments each can be initially linked to one another, and 4 intermediate products are therefore obtained. These intermediate products can then be used again in two separate linking reactions, and this therefore results in 2 extended intermediate products in turn, which are then linked to form the final product.

In one preferred embodiment, individual generated sequence segments, or sequence segment mixtures, or sequence segments, or sequence segment mixtures, which are already linked (intermediate products) are amplified by means of an additional PCR in order to increase the DNA amount for the further processing which follows. Here, it has to be ensured that the primers used for this purpose attach to the DNA sequence to be amplified again outside the mutation sites, if present.

In this way, it can be ensured that the variants of the variant library (linked DNA sequences) have essentially the same sequence length as the DNA starting sequence. In one preferred embodiment, the sequence length of the DNA sequences obtained (variants) deviate from the sequence length of the DNA starting sequence by not more than 10%, more preferably by not more than 7.5%, even more preferably by not more than 5%, yet even more preferably by not more than 2.5%, and in particular by not more than 1%. In a particularly preferred embodiment, the sequence length of the DNA sequences obtained (variants) is substantially identical to the sequence length of the DNA starting sequence.

Preferably, the DNA sequences of the variant library encode proteins or parts of proteins.

To isolate variants of the library, to express the library, and/or to select or to screen the variant library, it may be necessary to transfer the variant library into an organism. In a preferred embodiment, the method according to the invention therefore comprises the step:

e) cloning the variants into a suitable vector.

Vectors are transport agents for transferring foreign nucleic acids into a recipient cell. Vectors can be, for example, plasmids, viruses, or cosmids. Corresponding cloning methods for introducing the variant library into a vector are sufficiently known to persons skilled in the art.

A recipient organism can, for example, be transformed with the vector in order to subsequently express the corresponding proteins. The method according to the invention therefore preferably comprises the steps:

f) transfecting the vector into a suitable organism; and
g) expressing the proteins encoded by the respective variants.

Corresponding methods for the recombinant expression of proteins with the aid of host cells are sufficiently known to persons skilled in the art. However, alternatively, cell-free expression of the proteins can also be carried out. Corresponding methods for recombinant expression of proteins by means of cell-free in vitro translation extracts are sufficiently known to persons skilled in the art.

BRIEF DESCRIPTION OF THE DRAWINGS

The method according to the invention will be explained in further detail hereinafter with reference to the accompanying drawing figures.

DETAILED DESCRIPTION

Figure 1:
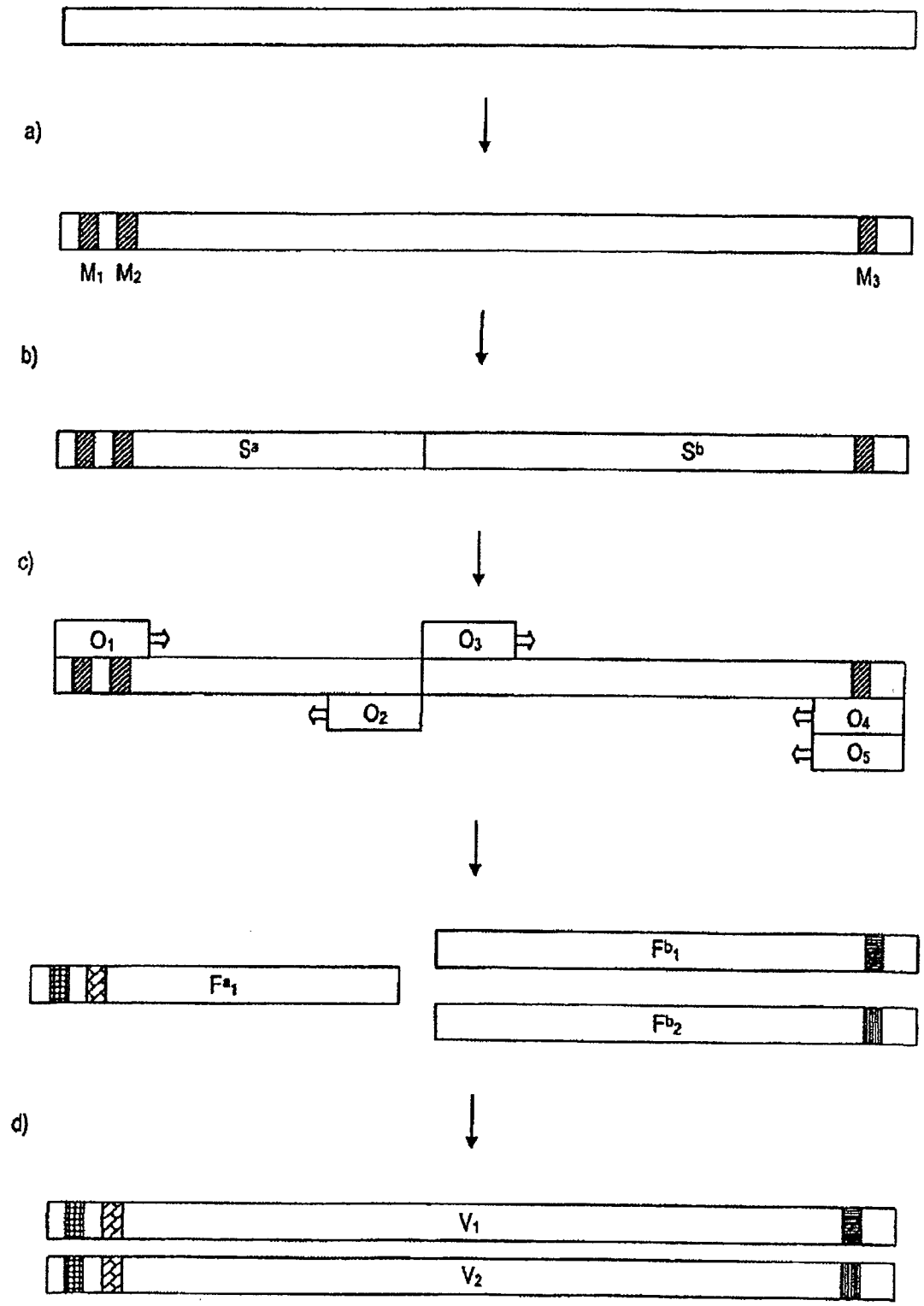
FIG. 1 is a schematic representation of a simple embodiment of the method according to the invention.

FIG. 1 schematically illustrates an especially simple embodiment of the method according to the invention. In step a), three mutation sites $M_1$, $M_2$, and $M_3$ are selected on the DNA starting sequence. In step b), the DNA starting sequence is divided into two sequence segments $S^a$ and $S^b$, where the sequence segment $S^a$ contains the mutation sites $M_1$ and $M_2$ and the sequence segment $S^b$ contains the mutation site $M_3$. In this exemplarily explained variant of the method, there are no sequence segments which do not contain a single mutation, but this is possible according to the invention. In step c), the two sequence segments $S^a$ and $S^b$ are amplified with the aid of the five oligonucleotides $O_1$, $O_2$, $O_3$, $O_4$, and $O_5$. The oligonucleotides $O_1$ and $O_3$ are sense primers and the oligonucleotides $O_2$, $O_4$, and $O_5$ are antisense primers, and this is indicated by the arrows and the structure above and below the starting sequence. Persons skilled in the art realize that the antisense primers bind to the DNA strand complementary to the DNA starting sequence. $O_1$, $O_4$, and $O_5$ are mismatch oligonucleotides and each bind at mutation sites; $O_2$ and $O_3$ are match oligonucleotides. $O_1$ introduces a mutation in each case at the mutation sites $M_1$ and $M_2$; $O_4$ and $O_5$ are in competition with one another and introduce a different mutation in each case at the mutation site $M_3$. Thus, amplification of sequence segment $S^a$ results in an individual fragment $F^a_1$, which has two mutations, and amplification of sequence segment $S^b$ results in two fragments $F^b_1$ and $F^b_2$, which each have one mutation, but are different from one another. The linking of the fragment $F^a_1$ with the fragment $F^b_1$ provides variant $V_1$, and the linking of the fragment $F^a_1$ with the fragment $F^b_2$ provides variant $V_2$ of the variant library. In this way, the method according to the invention generates a variant library of two variants which both differ from the DNA starting sequence (wild-type sequence) by exactly three mutations each.

Figure 2:
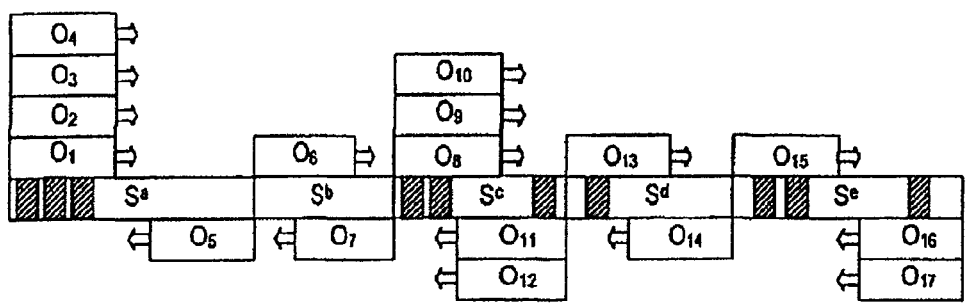
FIG. 2 is a schematic illustration of a more complex representative embodiment of the method of the invention.

FIG. 2 illustrates schematically a more complex situation, as can occur in the method according to the invention. Thus, the DNA starting sequence here is divided into five sequence segments $S^a$, $S^b$, $S^c$, $S^d$, and $S^e$. Sequence segments $S^a$, $S^c$, and $S^e$ each comprise three mutation sites, sequence segment $S^b$ does not comprise any mutation sites, and sequence segment $S^d$ comprises one mutation site. Oligonucleotides $O_1$ to $O_4$, $O_6$, $O_8$ to $O_{10}$, $O_{13}$, and $O_{15}$ are sense primers, and oligonucleotides $O_5$, $O_7$, $O_{11}$, $O_{12}$, $O_{14}$, $O_{16}$, and $O_{17}$ are antisense primers. Oligonucleotides $O_1$ to $O_4$, $O_8$ to $O_9$, $O_{11}$ and $O_{12}$, and $O_{16}$ and $O_{17}$ each compete with one another for mutation sites. Together with $O_{13}$, they are mismatch oligonucleotides. $O_5$ to $O_7$ and $O_{14}$ are match oligonucleotides.

A particular property of the method according to the invention can be explained in FIG. 2 in connection with the four oligonucleotides $O_1$, $O_2$, $O_3$, and $O_4$. It is possible for all four oligonucleotides to contain different mismatch positions for all three mutation sites on sequence segment $S^a$. However, it is also possible for the number of mismatch positions to vary, for example, for $O_1$ to introduce mutations at all three mutation sites, for $O_2$ to introduce mutations only at two mutation sites, for $O_3$ to introduce a mutation at only one mutation site, and for $O_4$ to introduce a mutation at another mutation site or to introduce no mutations ($O_4$ is, in the last case, not a mismatch oligonucleotide, but a match oligonucleotide). Suitable selection of the oligonucleotides thus makes it possible to establish the mutant distribution from the beginning very exactly, and this represents a particular advantage of the method according to the invention.

In the method according to the invention, there is at least one mutation site for which there is competition between at least 2 oligonucleotides, of which at least 1 oligonucleotide is a mismatch oligonucleotide, preferably both oligonucleotides are mismatch oligonucleotides.

In one preferred embodiment, there is in the method according to the invention at least one mutation site for which there is competition between at least 3 oligonucleotides, of which at least 2 oligonucleotides, preferably all oligonucleotides, are mismatch oligonucleotides.

In another preferred embodiment, there is in the method according to the invention at least one mutation site for which there is competition between at least 4 oligonucleotides, of which at least 3 oligonucleotides, preferably all oligonucleotides, are mismatch oligonucleotides.

In yet another preferred embodiment, there is in the method according to the invention at least one mutation site for which there is competition between at least 5 oligonucleotides, of which at least 4 oligonucleotides, preferably all oligonucleotides, are mismatch oligonucleotides.

Preferably, in the method according to the invention, there are at least two, more preferably at least three, even more preferably at least four, yet even more preferably at least five, and in particular at least six, mutation sites for which there is competition in each case between multiple oligonucleotides, of which preferably in each case at least one oligonucleotide is a mismatch oligonucleotide, more preferably all oligonucleotides are mismatch oligonucleotides.

Further preferred embodiments $A_1$ to $A_{30}$ of the method according to the invention are summarized in the following table:

|     | $A_1$ | $A_2$ | $A_3$ | $A_4$ | $A_5$ | $A_6$ | $A_7$ | $A_8$ | $A_9$ | $A_{10}$ |
|---|---|---|---|---|---|---|---|---|---|---|
| $M^{\geq 2}$ | ≥2 | ≥2 | ≥2 | ≥2 | ≥2 | ≥3 | ≥3 | ≥3 | ≥3 | ≥3 |
| $M^{\geq 3}$ | ≥1 | ≥1 | ≥1 | ≥1 | ≥1 | ≥1 | ≥1 | ≥1 | ≥1 | ≥1 |
| $M^{\geq 4}$ | ≥0 | ≥1 | ≥1 | ≥1 | ≥1 | ≥0 | ≥1 | ≥1 | ≥1 | ≥1 |
| $M^{\geq 5}$ | ≥0 | ≥0 | ≥1 | ≥1 | ≥1 | ≥0 | ≥0 | ≥1 | ≥1 | ≥1 |
| $M^{\geq 6}$ | ≥0 | ≥0 | ≥0 | ≥1 | ≥1 | ≥0 | ≥0 | ≥0 | ≥1 | ≥1 |
| $M^{\geq 7}$ | ≥0 | ≥0 | ≥0 | ≥0 | ≥1 | ≥0 | ≥0 | ≥0 | ≥0 | ≥1 |

|     | $A_{11}$ | $A_{12}$ | $A_{13}$ | $A_{14}$ | $A_{15}$ | $A_{16}$ | $A_{17}$ | $A_{18}$ | $A_{19}$ | $A_{20}$ |
|---|---|---|---|---|---|---|---|---|---|---|
| $M^{\geq 2}$ | ≥4 | ≥4 | ≥4 | ≥4 | ≥4 | ≥2 | ≥2 | ≥2 | ≥2 | ≥2 |
| $M^{\geq 3}$ | ≥1 | ≥1 | ≥1 | ≥1 | ≥1 | ≥2 | ≥2 | ≥2 | ≥2 | ≥2 |
| $M^{\geq 4}$ | ≥0 | ≥1 | ≥1 | ≥1 | ≥1 | ≥0 | ≥1 | ≥1 | ≥1 | ≥1 |
| $M^{\geq 5}$ | ≥0 | ≥0 | ≥1 | ≥1 | ≥1 | ≥0 | ≥0 | ≥1 | ≥1 | ≥1 |
| $M^{\geq 6}$ | ≥0 | ≥0 | ≥0 | ≥1 | ≥1 | ≥0 | ≥0 | ≥0 | ≥1 | ≥1 |
| $M^{\geq 7}$ | ≥0 | ≥0 | ≥0 | ≥0 | ≥1 | ≥0 | ≥0 | ≥0 | ≥0 | ≥1 |

|     | $A_{21}$ | $A_{22}$ | $A_{23}$ | $A_{24}$ | $A_{25}$ | $A_{26}$ | $A_{27}$ | $A_{28}$ | $A_{29}$ | $A_{30}$ |
|---|---|---|---|---|---|---|---|---|---|---|
| $M^{\geq 2}$ | ≥3 | ≥3 | ≥3 | ≥3 | ≥3 | ≥3 | ≥3 | ≥3 | ≥3 | ≥3 |
| $M^{\geq 3}$ | ≥2 | ≥2 | ≥2 | ≥2 | ≥2 | ≥3 | ≥3 | ≥3 | ≥3 | ≥3 |
| $M^{\geq 4}$ | ≥0 | ≥1 | ≥1 | ≥1 | ≥1 | ≥0 | ≥1 | ≥1 | ≥1 | ≥1 |
| $M^{\geq 5}$ | ≥0 | ≥0 | ≥1 | ≥1 | ≥1 | ≥0 | ≥0 | ≥1 | ≥1 | ≥1 |
| $M^{\geq 6}$ | ≥0 | ≥0 | ≥0 | ≥1 | ≥1 | ≥0 | ≥0 | ≥0 | ≥1 | ≥1 |
| $M^{\geq 7}$ | ≥0 | ≥0 | ≥0 | ≥0 | ≥1 | ≥0 | ≥0 | ≥0 | ≥0 | ≥1 |

"$M^{\geq 2}$" means a mutation site for which there is competition between at least two oligonucleotides, "$M^{\geq 3}$" means a mutation site for which there is competition between at least three oligonucleotides, and so on. This definition is cumulative, since one mutation site for which there is competition between, for example, four oligonucleotides is, at the same time, a mutation site for which there is competition between "at least 2", "at least 3", and "at least 4" oligonucleotides.

Thus, according to embodiment $A_4$ for example, there is one mutation site for which there is competition between at least 6 oligonucleotides and one mutation site for which there is competition between at least 2 oligonucleotides. Analogously, according to embodiment $A_{28}$, there is one mutation site for which there is competition between at least five oligonucleotides and two mutation sites for which there is competition in each case between at least three oligonucleotides.

Preferably, the number of different variants generated by the method according to the invention which are in the variant library is at least $10^1$, more preferably at least $10^2$, even more preferably at least $10^3$, yet even more preferably at least $10^4$, and in particular at least $10^5$. Each individual variant is represented at least once, but can also be represented multiple times.

The number of possible variants can be estimated by means of simple considerations. In regard to FIG. 2, there are four possibilities for the three mutation sites on sequence segment $S^a$ owing to the four oligonucleotides $O_1$, $O_2$, $O_3$, and $O_4$; three possibilities for the two mutation sites, depicted on the left, on sequence segment $S^c$ owing to the two oligonucleotides $O_8$, $O_9$, and $O_w$; two possibilities for the mutation site, depicted on the left, on sequence segment $S^c$ owing to the oligonucleotides $O_{11}$ and $O_{12}$; and likewise two possibilities for the mutation site, depicted on the right, on sequence segment $S^e$ owing to the oligonucleotides $O_{16}$ and $O_{17}$. For the remaining mutation sites, there is, in the absence of a competitive situation of multiple oligonucleotides, only a single possibility. The total number of possible variants is thus 4×3×2×2=48.

Preferably, the number K of variants present in total in the variant library can be exactly calculated according to the following formula: $K=(N_1 \times N_2 \times \ldots \times N_m)-W$, where m is the number of mutation sites, N is the number of permitted variants, including the optionally permitted wild-type sequence for a certain mutation site, and W is the amount of nonmutant sequences (wild-type sequences) of the variant library.

In one preferred embodiment, the method according to the invention is carried out in such a way that the variant library contains less than 1.0%, more preferably less than 0.5%, even more preferably less than 0.1%, yet even more preferably less than 0.05%, and in particular less than 0.01%, DNA starting sequences (wild-type sequences). In a particularly preferred embodiment, the method according to the invention is carried out in such a way that the variant library contains no (DNA starting sequences) wild-type sequences at all.

Preferably, the amount of nonmutant sequences W (wild-type sequences) of the variant library can be calculated via the following formula: $W=A_1 \times A_2 \times \ldots \times A_m$, where m is the number of mutation sites and A is the percentage amount of nonmutating oligonucleotides (match oligonucleotides) which is used for a certain mutation site. When the DNA starting sequence comprises, for example, 3 mutation sites, and there is competition for the first two mutation sites between 7 oligonucleotides, of which 6 oligonucleotides are mismatch oligonucleotides and one oligonucleotide is a match oligonucleotide, and there is competition for the third mutation site between five oligonucleotides, of which 4 oligonucleotides are mismatch oligonucleotides and one oligonucleotide is a match oligonucleotide, then this gives: $W=1/7 \times 1/7 \times 1/5=1/245 \approx 0.41\%$.

In one preferred embodiment, the variant library contains variants which have exactly the same number of mutations and mutation sites. More preferably, in the variant library generated by the method according to the invention, the number of variants which have exactly the same number of mutations and mutation sites is greater than the number of variants whose number of mutations is less by 1 than the number of mutation sites. Even more preferably, the number of variants whose number of mutations is less by 1 than the number of mutation sites is greater than the number of variants whose number of mutations is less by 2 than the number of mutation sites. Particularly preferably, for m mutation sites in total in the DNA starting sequence, the number of variants whose number of mutations is q is just as great or greater than the number of variants whose number of mutations is q−1, where q=1 to m.

In this regard, the mutant distribution can be set by the ratio of mismatch and match oligonucleotides. When, for example, two mismatch oligonucleotides and one match oligonucleotide compete for the same mutation site, the mismatch oligonucleotides generate mutations in the PCR, and the match oligonucleotide, in contrast, does not.

Preferably, the relative ratio of the variants which have just as many mutations as mutation sites to the variants whose number of mutations is less by 1 than the number of mutation sites is at least 55:45, more preferably at least 60:40, even more preferably at least 65:35, yet even more preferably at least 70:30, and in particular at least 75:25.

Preferably, the proportion of the variant fraction in the variant library increases with the number of mutations of the variants of the fraction.

Preferably, the largest variant fraction is the fraction having the largest number of mutations, and the library therefore does not contain any variant fractions which have more mutations than the largest variant fraction.

In one preferred embodiment, the method according to the invention is carried out such that, for at least 75%, more preferably at least 80%, even more preferably at least 85%, yet even more preferably at least 90%, and in particular at least 95%, of the variants generated in the variant library, the number of mutations per variant is in a range N, where $X \geq N > (X-5)$, where $X \in N$ and $35 > X > 5$. Preferably, for at least 75%, more preferably at least 80%, even more preferably at least 85%, yet even more preferably at least 90%, and in particular at least 95%, of the variants generated in the variant library, the number of mutations per variant is in a range N, where $X \geq N \geq (X-4)$, where $X \in N$ and $30 > X > 4$. More preferably, for at least 75%, more preferably at least 80%, even more preferably at least 85%, yet even more preferably at least 90%, and in particular at least 95%, of the variants generated in the variant library, the number of mutations per variant is in a range N, where $X \geq N \geq (X-3)$, where $X \in N$ and $25 > X > 3$. Even more preferably, for at least 75%, more preferably at least 80%, even more preferably at least 85%, yet even more preferably at least 90%, and in particular at least 95%, of the variants generated in the variant library, the number of mutations per variant is in a range N, where $X \geq N \geq (X-2)$, where $X \in N$ and $20 > X > 2$. Particularly preferably, for at least 75%, more preferably at least 80%, even more preferably at least 85%, yet even more preferably at least 90%, and in particular at least 95%, of the variants generated in the variant library, the number of mutations per variant is in a range N, where $X \geq N \geq (X-1)$, where $X \in N$ and $20 > X > 1$.

In one preferred embodiment, the method according to the invention is carried out such that the number of mutations per variant is the same in all variants of the variant library.

Figure 3:
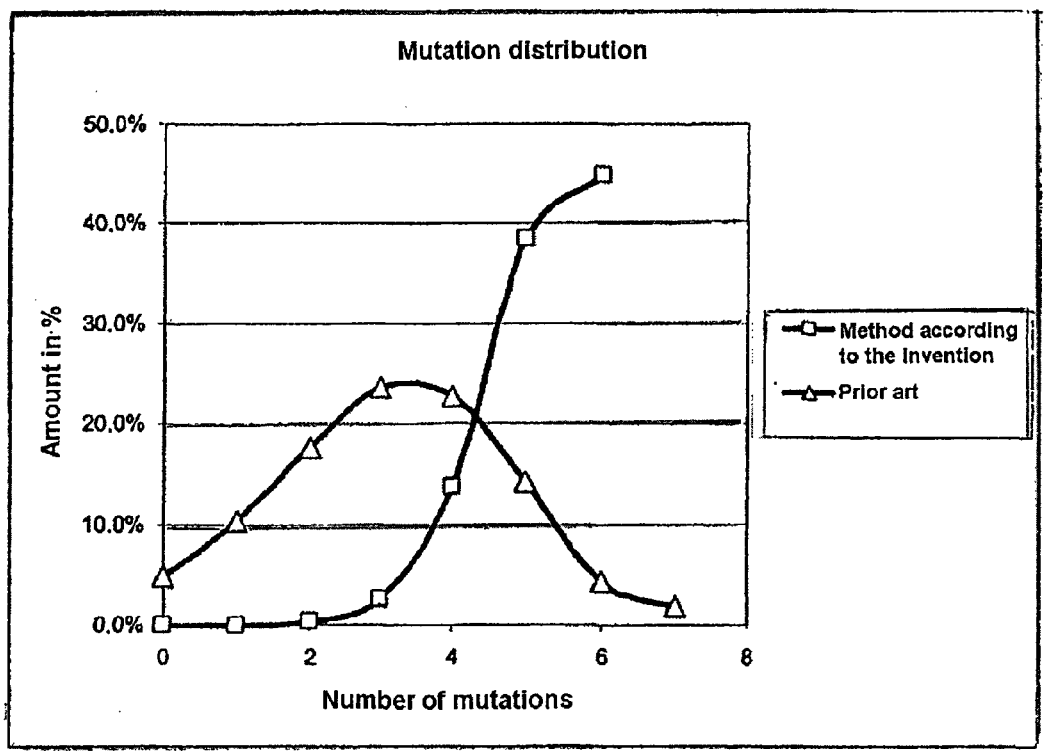
FIG. 3 is a depiction of the mutation distributions of two variant libraries.

FIG. 3 shows the mutation distributions of two variant libraries. One mutation distribution corresponds to a typical mutation distribution as can be generated when carrying out the method according to the invention. The second mutation distribution corresponds to a mutation distribution as can be typically generated by conventional methods of the prior art, such as error-prone PCR or massive mutagenesis for example.

The invention further relates to a variant library of a DNA sequence which is obtainable according to the method according to the invention.

The invention further relates to a variant library of a DNA sequence which has at least 3 mutation sites, wherein
 the variant library with respect to each mutation site contains in each case at least one variant which has at least one mutation at least this mutation site;
 the variant library does not contain variants which have more than 2 mutations, preferably more than 1 mutation, more than the number of mutations of the largest fraction of the variants; and
 the number of mutations of the largest fraction of the variants is ≥3.

The variant library according to the invention is characterized by a particular distribution of the mutations, wherein all variants having a certain number of mutations are subsumed under one fraction. The largest fraction of the variants has a number d of mutations. Purely theoretically, there are then smaller fractions of the variants which have d−1, d−2, d−3, . . . mutations, and smaller fractions of the variants which have d+1, d+2, d+3, . . . mutations. The variant library according to the invention is characterized in that it does not contain any variants which have d+3 or more mutations. Preferably, the variant library according to the invention is characterized in that it does not contain any variants which have d+2 or more mutations. Particularly preferably, the variant library according to the invention is characterized in that it does not contain any variants which have d+1 or more mutations.

In one preferred embodiment of the variant library according to the invention, the fraction of the variants which has d+2 mutations contains not more than 25% of the total number of variants in the variant library, more preferably not more than 20%, even more preferably not more than 15%, yet even more preferably not more than 10%, and in particular not more than 5%.

Particularly preferred embodiments $B_1$ to $B_{20}$ of the variant library according to the invention are summarized in the table below, wherein the largest fraction of the variants has a number m of mutations and the percentages indicate in each case the percentage content of the different variants of the fraction with respect to the total number of all different variants in the library:

|  | d | d + 1 | d + 2 |
|---|---|---|---|
| $B_1$ | ≥25% | ≤20% | ≤10% |
| $B_2$ | ≥25% | ≤15% | ≤10% |
| $B_3$ | ≥25% | ≤10% | ≤5% |
| $B_4$ | ≥25% | ≤5% | ≤1% |
| $B_5$ | ≥25% | ≤1% | ≤0.5% |
| $B_6$ | ≥30% | ≤20% | ≤10% |
| $B_7$ | ≥30% | ≤15% | ≤10% |
| $B_8$ | ≥30% | ≤10% | ≤5% |
| $B_9$ | ≥30% | ≤5% | ≤1% |
| $B_{10}$ | ≥30% | ≤1% | ≤0.5% |
| $B_{11}$ | ≥35% | ≤20% | ≤10% |
| $B_{12}$ | ≥35% | ≤15% | ≤10% |
| $B_{13}$ | ≥35% | ≤10% | ≤5% |
| $B_{14}$ | ≥35% | ≤5% | ≤1% |
| $B_{15}$ | ≥35% | ≤1% | ≤0.5% |
| $B_{16}$ | ≥40% | ≤20% | ≤10% |
| $B_{17}$ | ≥40% | ≤15% | ≤10% |
| $B_{18}$ | ≥40% | ≤10% | ≤5% |
| $B_{19}$ | ≥40% | ≤5% | ≤1% |
| $B_{20}$ | ≥40% | ≤1% | ≤0.5% |

The number of mutations d of the largest fraction is preferably at least 3, at least 4, at least 5, or at least 6, more preferably at least 7, at least 8, at least 9, or at least 10, even more preferably at least 11, at least 12, at least 13, or at least 14, yet even more preferably at least 15, at least 16, at least 17, or at least 18, and in particular at least 19, at least 20, at least 21, or at least 22.

Further preferred embodiments of the variant library according to the invention result from the abovedescribed preferred embodiments of the method according to the invention. These preferred embodiments apply correspondingly and are therefore not repeated at this point.

The following examples serve to explain the invention in further detail, but are not to be interpreted as being restrictive:

Example 1

The creation of a variant library using the method according to the invention will now be described. The starting sequence is an enzyme gene. Within the gene sequence, 6 mutation sites (1-6) which lie on 3 sequence segments in total were selected. A fourth sequence segment does not contain any mutation sites.

| Sequence segment | Size | Mutation site |
|---|---|---|
| I | 570 bp | — |
| II | 162 bp | 1-4 |
| III | 141 bp | 5 |
| IV | 251 bp | 6 |

| Mutation site | wt amino acid | Amino acids allowed |
|---|---|---|
| 1 | L | 4 (wt, K, R, M) |
| 2 | Y | 9 (wt, F, C, I, H, R, V, D, G) |
| 3 | W | 9 (wt, L, S, M, T, R, V, A, G) |
| 4 | N | 11 (wt, F, S, Y, C, I, T, V, A, D, G) |
| 5 | F | 4 (L, Q, V, E) |
| 6 | F | 6 (M, K, R, V, E, G) |

This results in a theoretical complexity of the library of 85,536 different protein variants.

| Mutation site | Mismatch primer | Match primer |
|---|---|---|
| 1 | 3 | 1 |
| 2-4 | 972* | 1 |
| 5 | 4 | 0 |
| 6 | 6* | 0 |

*Here, use was made of primer mixtures which were generated by the use of nucleotide mixtures in the oligonucleotide synthesis (degenerate primers)

Figure 4:
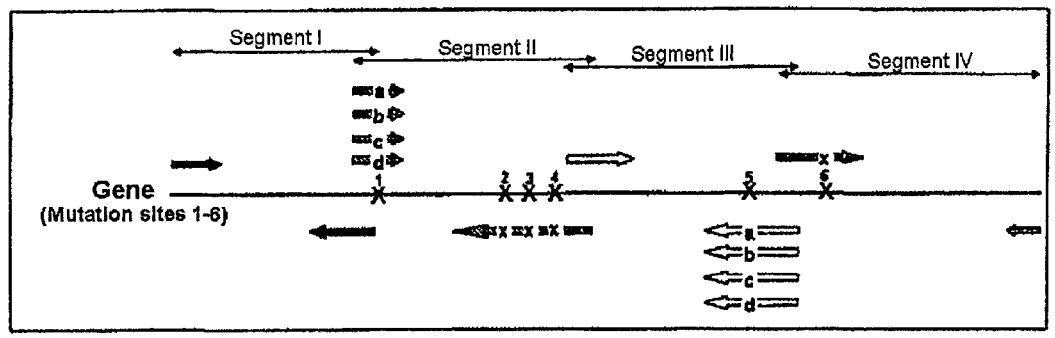
FIG. 4 is a schematic depiction of the sequence segments amplified by PCR.

PCR Amplification of the Fragments:

The sequence segments I to IV were amplified separately by PCR. As the case may be, mutations were specifically inserted into the respective mutation sites via mismatch primers. FIG. 4 shows schematically the sequence segments amplified by means of PCR. The arrows symbolize the primers used. Lower-case letters (a-d) represent mismatch primers having defined codons. The primers labeled with "x" are mismatch primers which were generated as degenerate primers.

Sequence Segment I
One PCR was carried out in which two primers without mutation sites were used.

Sequence Segment II
Four parallel PCRs were carried out by combining in each case three mismatch primers (a-c) or one match primer (d) for mutation site 1 with the degenerate primer mixture which covers the three mutation sites 2-4.

Sequence Segment III
Four parallel PCRs were carried out by combining a primer without mutation sites with four mismatch primers (a-d) for.

Sequence Segment IV
One PCR was carried out by combining a the degenerate primer mixture for mutation site 6 with a primer without mutation sites.

PCR with the DNA Polymerase FirePol:

| | |
|---|---|
| 10 µl | 10x B buffer (Solis BioDyne) |
| 10 µl | 25 mM MgCl$_2$ |
| 2 µl | dNTPs (each 10 mM) (Fermentas) |
| 1 µl | primer-fwd (100 mM) |
| 1 µl | primer-rev (100 mM) |
| 20 ng | plasmid having target gene |
| 10 U | FirePol (Solis BioDyne) |
| to 100 µl | distilled H$_2$O |

94° C., 1'30"/25 × (94° C., 20"/55° C., 20"/72° C., 45")/72° C., 10'

The four PCRs each for sequence segments II and III were quantified by means of agarose gel electrophoresis and mixed equimolarly in each case. The cleanup of all amplified fragments was carried out by agarose gel electrophoresis and extraction of the corresponding bands from the gel (gel cleanup kit, Promega).

Assembly of the Fragments
The assembly of the genes was carried out in this case by means of an overlap extension PCR. For this purpose, the fragments I-IV were mixed equimolarly and used in a PCR with the external primers of sequence segment I and IV.

Overlap Extension PCR with FirePol:

| | |
|---|---|
| 10 µl | 10x B buffer (Solis BioDyne) |
| 10 µl | 25 mM MgCl$_2$ |
| 2 µl | dNTPs (each 10 mM) (Fermentas) |
| 1 µl | primer-fwd (for fragment I, 100 mM) |
| 1 µl | primer-rev (for fragment IV, 100 mM) |
| 600 fmol | fragment I |
| 600 fmol | fragment II |
| 600 fmol | fragment III |
| 600 fmol | fragment IV |
| 10 U | FirePol (Solis BioDyne) |
| to 100 µl | distilled H$_2$O |

94° C., 30"/25 × (94° C., 20"/60° C., 20"/72° C., 1'10")/72° C., 10'

Cloning of the Sequences
The resulting fragment is cut directly with restriction endonucleases and cloned into the likewise cut expression vector pRSF-1b.

Restriction Digest Mixes

| Fragment: | | Vector: | |
|---|---|---|---|
| 2 µg | fragment | 5 µg | pRSF-1b |
| 5 µl | 10x O buffer (Fermentas) | 7 µl | 10x buffer Tango (Fermentas) |
| 25 U | PagI | 30 U | NcoI (Fermentas) |
| 15 U | PstI | 20 U | PstI (Fermentas) |
| to 50 µl | distilled H$_2$O | to 70 µl | distilled H$_2$O |

The restriction digest mixes are incubated at 37° C. for 2 h. After 1 h and 1.5 h, 1 U SAP (Fermentas) each are added to the "vector mix" for dephosphorylation. Subsequently, the enzymes are inactivated at 80° C. for 20 min. After that, the desired products are separated by means of agarose gel electrophoresis and cleaned up with the gel cleanup kit (Promega).

The vector DNA and the fragment are connected with one another as follows by incubation with T4 DNA ligase:
Ligase Mix:

| | | |
|---|---|---|
| 200 fmol | | vector DNA |
| 600 fmol | | fragment |
| 1 µl | | 10x ligase buffer (Fermentas) |
| 1 U | | T4 DNA ligase (Fermentas) |
| to 10 µl | | distilled H$_2$O |

The mixes are incubated at 16° C. for 12 hours, and the ligase was subsequently inactivated by heating for 10 minutes to 65° C. The ligation mix was cleaned up by means of phenol-chloroform extraction and concentrated by means of ethanol precipitation. The mix was directly used to transform XL1-Blue *E. coli* cells (Stratagene) by means of electroporation. To determine the clone number achieved, some of the electroporated cells were spread out on LB/kanamycin agar plates for counting, whereas the rest of the transformation mix was grown overnight in liquid LB/kanamycin medium at 37° C. and 200 rpm. Starting from this culture, the plasmid library was obtained by means of a midi plasmid preparation with the aid of a purification kit (Macherey+Nagel). By counting the individual clones on the agar plates, the complexity of the library was determined to be 223 000 clones. Thus, the theoretical library size was covered 2.6 times. From 10 individual colonies, the plasmid was isolated by means of a plasmid mini preparation kit (M+N), and the enzyme gene present was characterized by sequencing.

Sequencing of 10 Individual Clones of the Library

| | Mutation site | | | | | |
|---|---|---|---|---|---|---|
| | 1 | 2 | 3 | 4 | 5 | 6 |
| wt | Leu | Tyr | Trp | Asn | Phe | Phe |
| Clone 1 | Met | Leu | Trp | Cys | Val | Lys |
| Clone 2 | Met | Gly | Leu | Ile | Gln | Arg |
| Clone 3 | Leu | Tyr | Gly | Ile | Val | Lys |
| Clone 4 | Lys | Phe | Val | Asn | Gln | Lys |
| Clone 5 | Met | Arg | Ala | Ile | Leu | Met |
| Clone 6 | Met | Tyr | Ala | Ser | Glu | Lys |
| Clone 7 | Arg | Phe | Val | Gly | Glu | Lys |
| Clone 8 | Lys | Phe | Leu | Cys | Glu | Arg |
| Clone 9 | Lys | Asp | Gly | Phe | Gln | Gly |
| Clone 10 | Met | Val | Met | Phe | Leu | Lys |
| Mutation | 1× Leu | 2× Phe | 2× Leu | 2× Phe | 2× Leu | 1× Met |
| distribution | 3× Lys | 2× Tyr | 0× Ser | 1× Ser | 3× Gln | 6× Lys |
| | 1× Arg | 1× Cys | 1× Trp | 0× Tyr | 2× Val | 2× Arg |
| | 5× Met | 1× Leu | 1× Met | 2× Cys | 3× Glu | 0× Val |
| | | 1× Arg | 0× Thr | 3× Ile | | 0× Glu |
| | | 0× His | 0× Arg | 0× Thr | | 1× Gly |
| | | 1× Val | 2× Val | 1× Asn | | |
| | | 1× Asp | 2× Ala | 1× Ala | | |
| | | 1× Gly | 2× Gly | 0× Val | | |
| | | | | 0× Asp | | |
| | | | | 1× Gly | | |

Figure 5:
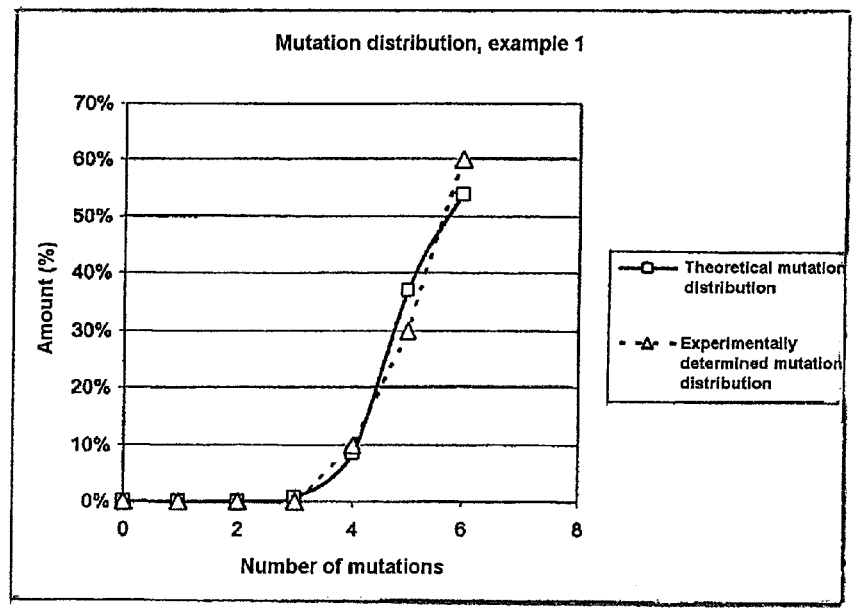
FIG. 5 is a graph of the expected sequence distribution for example 1.

Thus, 6 variants having 6 amino acid mutations were found, 3 variants having 5 mutations were found, and 1 variant having four mutations was found. None of the variants had fewer than 4 mutations. The resulting mutation distribution corresponds very well to the theoretically expected distribution as shown in FIG. 5.

Example 2

In this example, the creation of an enzyme variant library using the method according to the invention is described. The starting sequence is the gene for lipase B from *Candida antarctica* (CalB). Within the gene sequence, 5 amino acids to be mutated (K32, Q58, R242, R249, E269) which lie on 5 sequence segments in total were selected.

| Sequence segment | Size | Mutation site (amino acid) |
|---|---|---|
| I | 167 bp | K32 |
| II | 99 bp | Q58 |
| III | 570 bp | R242 |
| IV | 78 bp | R249 |
| V | 396 bp | E269 |

| wt amino acid | Amino acids allowed |
|---|---|
| K32 | 11 (wt, P, L, F, W, S, Y, E, Q, G, A) |
| Q58 | 11 (wt, P, L, F, W, S, Y, E, R, G, A) |
| R242 | 11 (wt, P, L, F, W, S, Y, E, Q, G, A) |
| R249 | 11 (wt, P, L, F, W, S, Y, E, Q, G, A) |
| E269 | 11 (wt, P, L, F, W, S, Y, R, Q, G, A) |

This results in a theoretical complexity of the library of 161,051 different protein variants.

PCR Amplification of the Fragments:

The sequence segments I to V were amplified separately by PCR. As the case may be, mutations were specifically inserted into the respective mutation sites via mismatch primers. For each of the five sequence segments, 11 parallel PCRs were carried out by combining in each case 10 mismatch primers or one match primer (wt) for the mutation site with a primer without mutation sites.

Sequence Segments I to V

PCR with the DNA Polymerase Phusion™ Hot Start:

| | |
|---|---|
| 20 µl | 5x HF buffer (Finnzymes) |
| 2 µl | dNTPs (each 10 mM) (Fermentas) |
| 5 µl | primer-fwd (10 mM) |
| 5 µl | primer-rev (10 mM) |
| 20 ng | plasmid DNA having target gene |
| 2 U | Phusion ™ Hot Start (Finnzymes) |
| to 100 µl | distilled H$_2$O |

98° C., 30"/30 × (98° C., 10"/65° C., 20"/72° C., 10")/72° C., 10'

The 11 PCRs each for sequence segments I to V were quantified by agarose gel electrophoresis and mixed equimolarly in each case. The cleanup of all amplified fragments was carried out by agarose gel electrophoresis and extraction of the corresponding bands from the gel (gel cleanup kit, Promega).

Assembly of the Fragments

The assembly of the genes was carried out in the example by an overlap extension PCR. For this purpose, the fragments I-V were mixed equimolarly and used in a PCR with the external primers of sequence segments I and V.

Overlap Extension PCR with PfuUltra™ HF DNA Polymerase:

| | |
|---|---|
| 10 µl | 10x PfuUltra ™ HF buffer (Stratagene) |
| 2 µl | dNTPs (each 10 mM) (Fermentas) |
| 2.5 µl | primer I-fwd (10 mM) |
| 2.5 µl | primer V-rev (10 mM) |
| 600 fmol | fragment I |
| 600 fmol | fragment II |
| 600 fmol | fragment III |

-continued

| | | |
|---|---|---|
| 600 fmol | fragment IV | |
| 600 fmol | fragment V | |
| 2.5 U | PfuUltra ™ (Stratagene) | |
| to 100 µl | distilled H$_2$O | |

95° C., 2'/20 × (95° C., 30"/54° C., 30"/72° C., 1'30")/72° C., 10'

Cloning of the Sequences

The resulting fragment is cut directly with restriction endonucleases and cloned into the likewise cut expression vector pEXP.

Restriction Digest Mixes:

| Fragment: | | Vector: | |
|---|---|---|---|
| 5 µg | fragment | 20 µg | pEXP |
| 20 µl | 10x R buffer (Fermentas) | 40 µl | 10x R buffer (Fermentas) |
| 30 U | XhoI (Fermentas) | 240 U | XhoI (Fermentas) |
| 20 U | NotI (Fermentas) | 100 U | NotI (Fermentas) |
| to 200 µl | distilled H$_2$O | to 400 µl | distilled H$_2$O |

The restriction digest mixes are incubated at 37° C. for 12 h. After 11 h and 11.5 h, 4 U CIAP (Fermentas) each are added to the "vector mix" for dephosphorylation. Subsequently, the enzymes are inactivated by phenol-chloroform extraction. After that, the desired products are separated by means of agarose gel electrophoresis and cleaned up with the gel cleanup kit (Promega).

The vector DNA and the fragment are connected with one another as follows by incubation with T4 DNA ligase:

Ligase Mix:

| | |
|---|---|
| 500 fmol | vector DNA |
| 1500 fmol | fragment |
| 6 µl | 10x ligase buffer (Fermentas) |
| 15 U | T4 DNA ligase (Fermentas) |
| to 60 µl | distilled H$_2$O |

The mixes are incubated at 16° C. for 10 h, and the ligase was subsequently inactivated by heating for 15 minutes to 65° C. The ligation mix was cleaned up by means of phenol-chloroform extraction and concentrated by means of ethanol precipitation. The mix was directly used to transform XL1-Blue *E. coli* cells (Stratagene) by means of electroporation. To determine the clone number achieved, some of the electroporated cells were spread out on selection LB agar plates for counting, whereas the rest of the transformation mix was grown overnight in liquid selection LB medium at 30° C. and 200 rpm. Starting from this culture, the plasmid library was obtained by means of a midi plasmid preparation with the aid of a purification kit (Macherey+Nagel). By counting the individual clones on the agar plates, the complexity of the library was determined to be 1.33 million clones. Thus, the theoretical library size was covered 8.3 times. From 10 individual colonies, the plasmid was isolated by means of a plasmid mini preparation kit (M+N) and the enzyme gene present was characterized by sequencing.

Sequencing of 10 Individual Clones of the Library

| Mutation site | K32 | Q58 | R242 | R249 | E269 |
|---|---|---|---|---|---|
| CalB wt | K | Q | R | R | E |
| Clone 1 | G | A | S | P | W |
| Clone 2 | Q | A | G | W | W |
| Clone 3 | Q | S | Y | Y | S |
| Clone 4 | S | S | G | S | Y |
| Clone 5 | S | R | Y | W | W |
| Clone 6 | Q | E | S | F | A |
| Clone 7 | E | S | Y | R | F |
| Clone 8 | E | Q | W | F | W |
| Clone 9 | E | P | L | Q | E |
| Clone 10 | W | W | W | R | P |
| Mutation distribution | 0xK | 1xQ | 0xR | 2xR | 1xE |
| | 0xP | 1xP | 0xP | 1xP | 1xP |
| | 0xL | 0xL | 1xL | 0xL | 0xL |
| | 0xF | 0xF | 0xF | 2xF | 1xF |
| | 1xW | 1xW | 2xW | 2xW | 4xW |
| | 2xS | 3xS | 2xS | 1xS | 1xS |
| | 0xY | 0xY | 3xY | 1xY | 1xY |
| | 3xE | 1xE | 0xE | 0xE | 0xR |
| | 3xQ | 1xR | 0xQ | 1xQ | 0xQ |
| | 1xG | 0xG | 2xG | 0xG | 0xG |
| | 0xA | 2xA | 0xA | 0xA | 1xA |

Thus, 6 variants having 5 amino acid mutations and 4 variants having 4 mutations were obtained. None of the variants had fewer than 4 mutations.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the amended claims and equivalents thereof.

The invention claimed is:

1. A method for generating a library of DNA variants starting from one DNA starting sequence, using primer pairs and site directed mutagenesis in polymerase chain reactions (PCR) to amplify segments of the DNA starting sequence, wherein at least two of the amplified segments have a mutation introduced in preselected nucleotide positions by site directed mutagenesis, and wherein the amplified segments are ligated together to produce a library of DNA variants each variant consisting of the sequence of the DNA starting sequence except for the mutations introduced by PCR, the method comprising, a) pre-selecting at least two partial sequences of the DNA starting sequence to be mutated (each partial sequence comprising a "mutation site") on the DNA starting sequence;

b) identifying at least two contiguous segments of the DNA starting sequence, such that the segments in sum comprise the entirety of the DNA starting sequence, wherein at least two of the segments comprise the mutation site, and wherein no mutation site is present in more than one segment, c) designing an oligonucleotide primer pair for amplifying each of said segments, the designing of the primers is such that, for each segment said primer pair comprises a sense and antisense primer complementary to the 3' and 5' terminal sequences of the segment, and such that
(1) for the at least two segments having the mutation site, the sense and/or antisense primer of each primer pair is a mismatch primer that spans the mutation site, and
(2) for at least one of the segments having the mutation site, at least two primer pairs are designed each constituting a type of primer pair, the designing being such that one primer is common to the at least two primer pairs, and the other primer of each of the at least two primer pairs is a mismatch primer that spans the mutation site, wherein none of the at least two primer pairs comprise the same mismatch primer,
(3) the primers further comprise 5'-terminal sequences, that allow orientation-specific linking of PCR amplification products in subsequent step e)(2) through
(i) oligonucleotide design of the sense and antisense primers of contiguous segments to provide overlapping oligonucleotide regions that hybridize in overlap extension PCR in subsequent step e)(2), or
(ii) oligonucleotide design of sense and antisense primers of contiguous segments such that the contiguous segments comprise orientation-specific restriction enzyme cleavage sites that restore the DNA starting sequence in restriction cleavage and segment linkage in subsequent step e)(2),
d) amplifying all of the contiguous segments of the DNA starting sequence by,
(1) distributing each primer pair of (c) to a vessel such that no vessel comprises more than one of the type of primer pair and adding the DNA starting sequence to each vessel,
(2) performing PCR on the DNA starting sequence and primer pairs in the vessels thereby producing an amplified segment of the DNA starting sequence in each vessel,
e) producing a library of DNA molecules (each a variant), wherein the sequence of each variant is identical to the sequence of the DNA starting sequence except for the mutations introduced during the PCR amplification, by,
(1) isolating the amplified segments from each vessel of d)(2),
(2) linking together the amplified segments of e)(1) in consecutive order by extension PCR or by digesting the amplified segments with restriction enzymes that cleave the restriction sites introduced by the oligonucleotides and subsequently ligating the digested segments with a ligase, to produce variants, each variant consisting of a nucleotide sequence that is identical to the DNA starting sequence except for the mutations introduced during the PCR amplification.

2. The method as claimed in claim 1, wherein at least one segment does not comprise a preselected mutation site.

3. The method as claimed in claim 1, wherein at least one segment comprises more than one mutation site.

4. The method as claimed in claim 3, wherein the sense oligonucleotide is a mismatch primer that spans one of the mutation sites and the anti-sense oligonucleotide is a mismatch oligonucleotide that spans another one of the mutation sites.

5. The method as claimed in claim 1, wherein the amplification products in step d) (2) are quantified and mixed before they are linked in step e)(2).

6. The method as claimed in claim 1, wherein the number of variants produced in step (e) having a sequence that differs from the DNA starting sequence at all the mutation sites is greater than the number of variants having a sequence that differs from the DNA starting sequence at at least one but not all mutation sites.

7. The method as claimed in claim 1, wherein the variant library contains less than 1.0% DNA starting sequences.

8. The method as claimed in claim 1, wherein for at least 75% of the variants in the library, the number of changes at mutation sites per variant is in the range N; where $X \geq N \geq (X-2)$ with $X \in N$ and $20 > X > 2$.

9. The method as claimed in claim 1, wherein, for at least 75% of the variants in the variant library, the number of mutations per variant is in the range N, where $X \geq N \geq (X-1)$ with $X \in N$ and $20 > X > 1$.

10. The method as claimed in claim 1, wherein the sense primer or the anti-sense primer is a match-primer that spans one of the mutation sites.

* * * * *